(12) United States Patent
Xu

(10) Patent No.: US 11,700,901 B2
(45) Date of Patent: Jul. 18, 2023

(54) GOGGLES

(71) Applicant: SHENZHEN CYLION TECHNOLOGY INTL CO., LTD., Shenzhen (CN)

(72) Inventor: Bo-Jie Xu, Shenzhen (CN)

(73) Assignee: SHENZHEN CYLION TECHNOLOGY INTL CO., LTD., Shenzhen (CN)

( * ) Notice: Subject to any disclaimer, the term of this patent is extended or adjusted under 35 U.S.C. 154(b) by 129 days.

(21) Appl. No.: 17/102,998

(22) Filed: Nov. 24, 2020

(65) Prior Publication Data
US 2021/0153587 A1    May 27, 2021

(30) Foreign Application Priority Data

Nov. 27, 2019  (CN) .......................... 201911183274.8

(51) Int. Cl.
*A42B 1/247* (2021.01)
*A61F 9/02* (2006.01)

(52) U.S. Cl.
CPC .............. *A42B 1/247* (2013.01); *A61F 9/025* (2013.01)

(58) Field of Classification Search
CPC . A42B 1/247; A42B 3/185; A61F 9/02; A61F 9/025; A61F 9/029
See application file for complete search history.

(56) References Cited

U.S. PATENT DOCUMENTS

| | | | | |
|---|---|---|---|---|
| 3,051,957 A | * | 9/1962 | Chan ........................ | G02C 3/02 2/444 |
| 3,563,640 A | * | 2/1971 | Wise et al. ........... | A62B 18/082 128/201.12 |
| 4,810,080 A | * | 3/1989 | Grendol ................. | G02C 11/12 351/158 |
| 5,170,502 A | * | 12/1992 | Hegendorfer ............ | G02C 9/04 2/13 |
| 5,371,555 A | * | 12/1994 | Nagel ....................... | A61F 9/02 351/158 |
| 5,657,106 A | * | 8/1997 | Herald, Jr. .............. | A61F 9/025 351/158 |
| 5,764,332 A | * | 6/1998 | Kranhouse .............. | B63C 11/12 351/41 |
| 5,790,230 A | * | 8/1998 | Sved ....................... | A61F 9/025 351/110 |

(Continued)

*Primary Examiner* — F Griffin Hall
(74) *Attorney, Agent, or Firm* — Karin L. Williams; Mayer & Williams PC

(57) ABSTRACT

Goggles include a frame unit having a main hole and a connecting portion, an adjustment set disposed on the frame unit, a first lens unit pivotally disposed on the frame unit, and a second lens unit having an engagement portion pivotally connected to the adjustment set. The adjustment set has an adjusting unit penetrating through the main hole, a positioning unit engaging with the adjusting unit, and a positioning hole formed on the positioning unit and adapted to engage with the engagement portion. Accordingly, the first lens unit can be lifted open at any angle relative to the frame unit. The upward and downward movement of the second lens unit is adjusted by the adjustment set, and a rotation of the engagement portion within the positioning hole allows the second lens unit to be lifted open at any angle relative to the frame unit.

6 Claims, 5 Drawing Sheets

(56) References Cited

U.S. PATENT DOCUMENTS

| | | | | |
|---|---|---|---|---|
| 5,802,622 | A * | 9/1998 | Baharad | A61F 9/02 2/2.5 |
| 5,929,963 | A * | 7/1999 | McNeal | G02C 9/04 351/57 |
| 6,357,053 | B1 * | 3/2002 | Wang-Lee | A61F 9/025 2/431 |
| 7,058,991 | B2 * | 6/2006 | Hartman | A61F 9/025 2/437 |
| 7,370,374 | B2 * | 5/2008 | Penque, Jr. | A61F 9/028 2/431 |
| 7,431,453 | B2 * | 10/2008 | Hogan | A61F 9/025 351/158 |
| 7,637,611 | B1 * | 12/2009 | Rotella | G02C 3/02 351/158 |
| 7,641,333 | B2 * | 1/2010 | Blanshay | G02C 9/00 351/57 |
| 8,113,200 | B2 * | 2/2012 | Davis | A62B 18/02 128/206.13 |
| 8,601,617 | B1 * | 12/2013 | Krnc | A62B 18/08 2/443 |
| 10,463,091 | B2 * | 11/2019 | Bourque | A41D 13/11 |
| 2007/0261155 | A1 * | 11/2007 | Tabacchi | A61F 9/025 2/439 |
| 2011/0083256 | A1 * | 4/2011 | Wang-Lee | G02C 9/04 2/434 |
| 2013/0014316 | A1 * | 1/2013 | Castro | G02C 11/00 2/427 |
| 2017/0216099 | A1 * | 8/2017 | Saladino | A42B 1/048 |

* cited by examiner

GOGGLES

BACKGROUND OF THE INVENTION

1. Field of the Invention

This invention relates to an eye protecting device and relates particularly to goggles.

2. Description of the Related Art

In order to prevent a rider's view and breath from being obstructed by wind and sand during driving a bicycle or a motorcycle, a head cover and windproof glasses are usually adapted to protect and cover the rider's mouth, nose and eyes. However, when the mouth and the nose are covered, the rider cannot breathe smoothly, and that affects the comfort in use. Further, the head cover and the windproof glasses cannot be in close contact with a nose bridge of the rider, and that causes the windproof glasses to fog up because exhaled air from the rider's breath will be directed upwards to contact with lenses of the windproof glasses. These problems need to be improved.

Furthermore, the windproof glasses are usually designed for riders having myopia. The windproof glasses are generally equipped with an outer lens unit for attaining a windproof effect and an inner lens unit which includes optical lenses for myopia or astigmatism. However, the inner lens unit is usually fixed to a frame unit of the windproof glasses directly, and that causes a position of the inner lens unit to be unable to be adjusted upwards or downwards. Meanwhile, the inner lens unit cannot be lifted open. Thus, the rider cannot adjust the outer lens unit and the inner lens unit while wearing the windproof glasses, and that increases the discomfort and inconvenience of wear and needs to be improved.

SUMMARY OF THE INVENTION

The object of this invention is to provide goggles capable of achieving multiple adjustment and increasing convenience of use.

The goggles include a frame unit, an adjustment set disposed on the frame unit, a first lens unit pivotally disposed on the frame unit, and a second lens unit disposed on the adjustment set. The frame unit has a connecting portion connected to the first lens unit and a main hole formed on the frame unit. The second lens unit has an engagement portion engaging with the adjustment set. The adjustment set has an adjusting unit penetrating through the main hole of the frame unit, a positioning unit engaging with the adjusting unit, and a positioning hole formed on the positioning unit. The engagement portion of the second lens unit is adapted to be rotatably inserted in the positioning hole of the positioning unit to thereby connect the second lens unit to the adjustment set pivotally. Thus, the first lens unit can be lifted open at any angle relative to the frame unit for adjustment. The upward and downward movement of the second lens unit is adjusted through the adjustment set. A rotation of the engagement portion within the positioning hole allows the second lens unit to be lifted open at any angle relative to the frame unit to thereby achieve multiple adjustment and increase the convenience of use. Further, the goggles can be connected to a head cover for protecting a human face properly to thereby attain the effect of being windproof and sandproof.

Preferably, a first hole and a second hole communicating with the first hole are respectively formed on the positioning unit. The adjusting unit is inserted into the first hole. The first hole penetrates through the positioning unit by a first penetrating direction. The second hole penetrates through the positioning unit by a second penetrating direction. The first penetrating direction of the first hole is perpendicular to the second penetrating direction of the second hole. A locking unit is disposed in the second hole and adapted to engage with the adjusting unit of the adjustment set to thereby adjust a position of the second lens unit.

Preferably, a nose supporting unit is disposed on the frame unit for fitting a nose bridge of a human while wearing the goggles and an elastic pad is disposed on a periphery of the frame unit for being in close contact with a human face while wearing the goggles.

Preferably, an elastic belt is connected to the frame unit and a regulating buckle is disposed on the elastic belt and adapted to adjust a length of the elastic belt.

Preferably, a head cover is connected to the goggles. The head cover has a visual region and a breathing region. The goggles are installed on the visual region. A periphery of the goggles fits a periphery of the visual region for a close engagement.

Preferably, the head cover has an elastic rope and a fixing buckle for adjusting an open scope of the visual region. The elastic rope is disposed beside the visual region and positioned by the fixing buckle.

Preferably, a breathing mask is disposed on the breathing region. The breathing mask is situated at a place corresponding to a human nose while wearing the head cover.

DETAILED DESCRIPTION OF THE PREFERRED EMBODIMENTS

Figure 1:
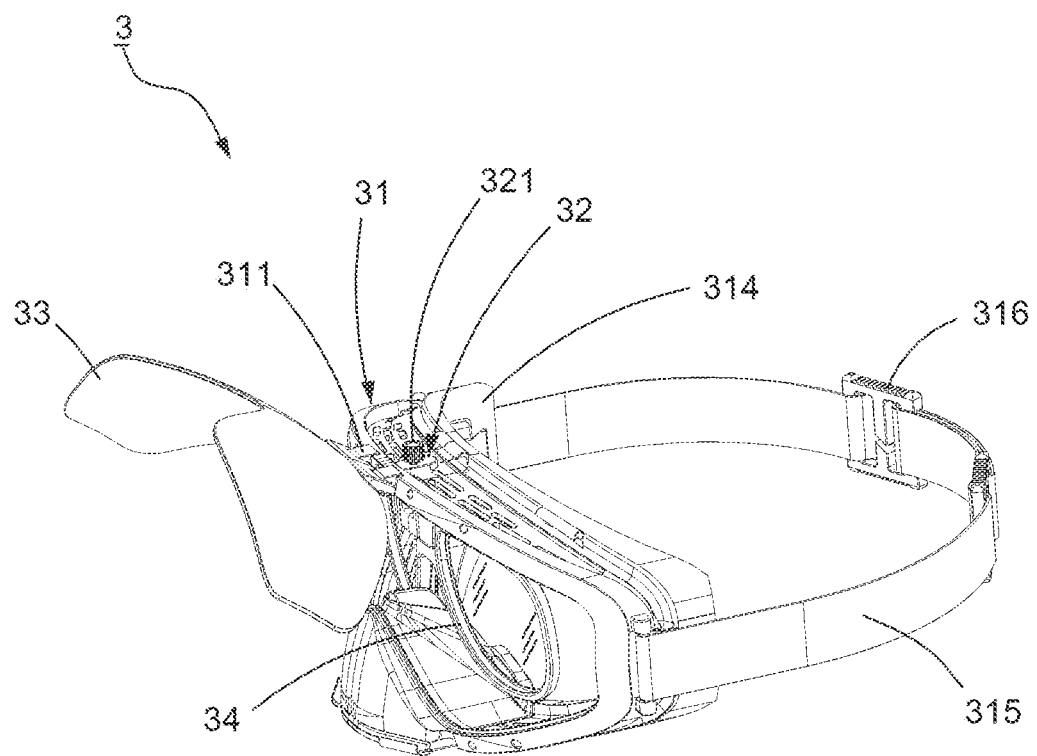
FIG. 1 is a perspective view showing a first preferred embodiment of this invention.
Figure 2:
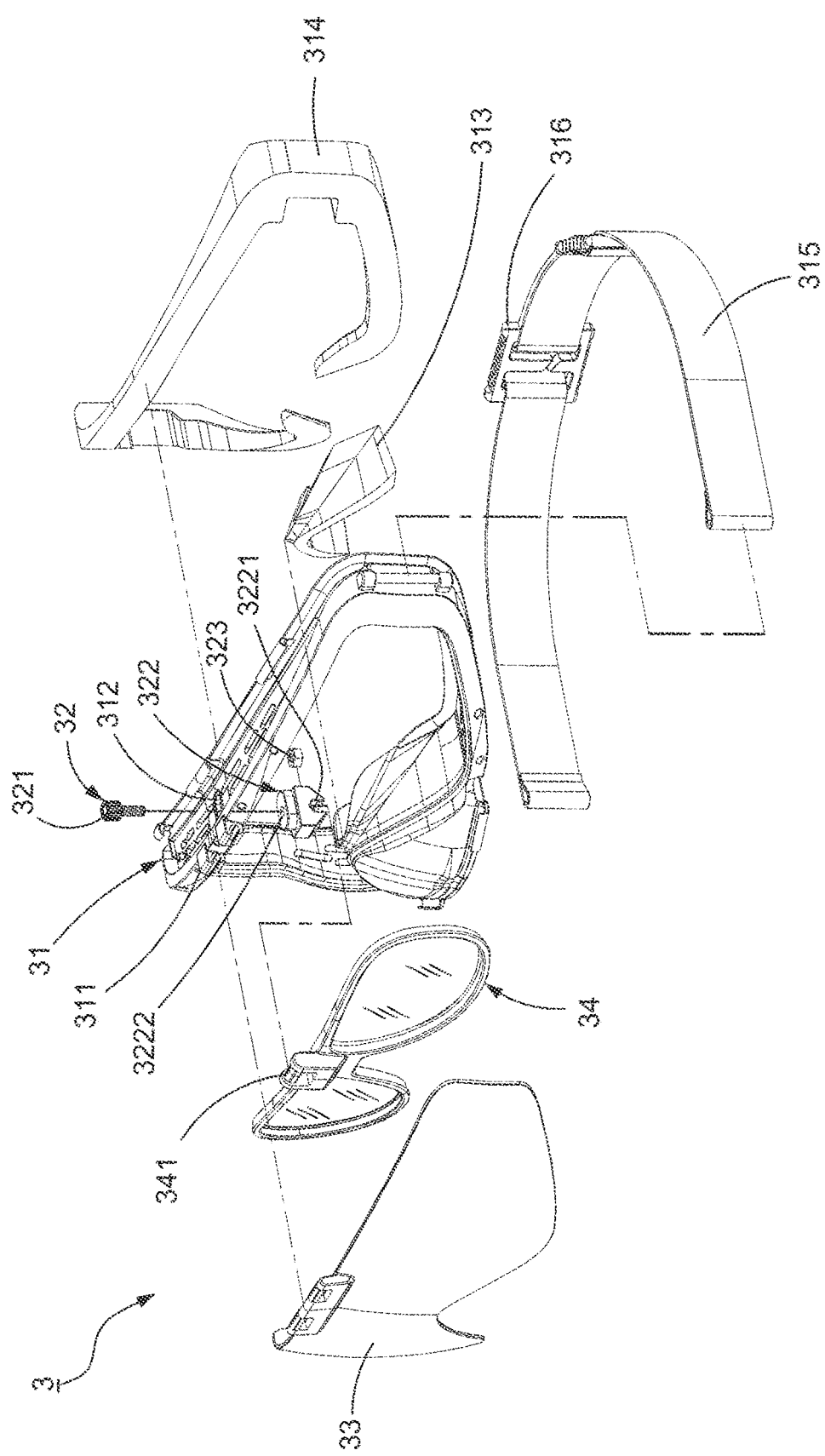
FIG. 2 is an exploded view showing the first preferred embodiment of this invention.

Referring to FIG. 1 and FIG. 2, a first preferred embodiment of goggles 3 is disclosed. The goggles 3 in this preferred embodiment include a frame unit 31, an adjustment set 32 disposed on the frame unit 31, a first lens unit 33 pivotally disposed on the frame unit 31, and a second lens unit 34 disposed on the adjustment set 32. Lenses of the first lens unit 33 are made from materials capable of shedding wind and sand to thereby attain the protection effect of being windproof and sandproof. Lenses of the second lens unit 34 are optical lenses which can correct nearsightedness to thereby fit the requirements of users having myopia and astigmatism. In this preferred embodiment, the second lens unit 34 has an engagement portion 341 adapted to engage with the adjustment set 32.

Figure 3:
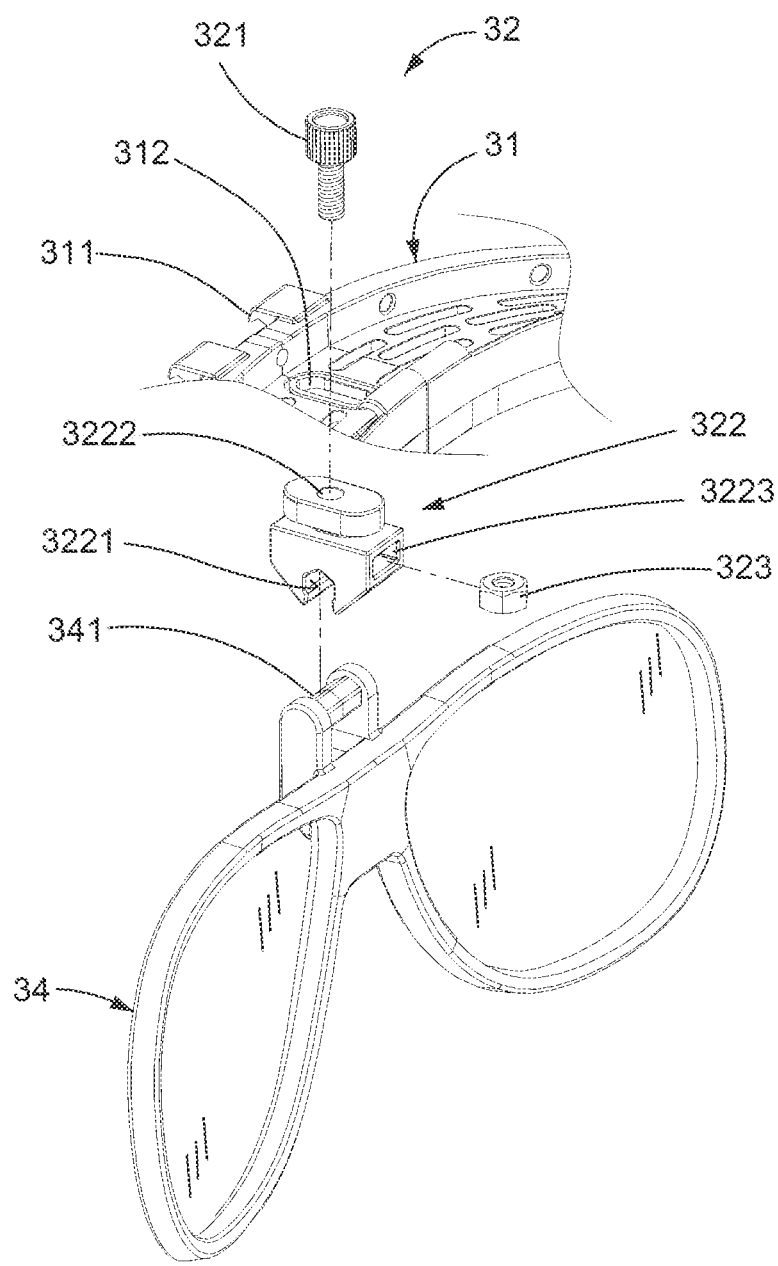
FIG. 3 is an exploded view showing the installation of the second lens unit and the adjustment set.

The frame unit 31 has a connecting portion 311 to which the first lens unit 33 is connected and forms a main hole 312 adapted to engage with the adjustment set 32. The first lens unit 33 is pivotally disposed on the connecting portion 311 to allow the first lens unit 33 to be lifted open at any angle relative to the frame unit 31. Referring to FIG. 3, the adjustment set 32 has an adjusting unit 321 penetrating through the main hole 312 of the frame unit 31 and a positioning unit 322 engaging with the adjusting unit 321. A positioning hole 3221 is formed on the positioning unit 322. The engagement portion 341 of the second lens unit 34 is adapted to be rotatably inserted in the positioning hole 3221 to thereby connect the second lens unit 34 to the adjustment set 32 pivotally. Thus, the second lens unit 34 can be lifted open at any angle relative to the frame unit 31 by rotating the engagement portion 341 within the positioning hole 3221 to thereby allow the second lens unit 34 to be inclined to the frame unit 31.

The positioning unit 322 has a first hole 3222 and a second hole 3223 communicating with the first hole 3222. The adjusting unit 321 is inserted into the first hole 3222. The first hole 3222 penetrates through the positioning unit 322 by a first penetrating direction. The second hole 3223 penetrates through the positioning unit 322 by a second penetrating direction. The first penetrating direction of the first hole 3222 is perpendicular to the second penetrating direction of the second hole 3223. A locking unit 323 is disposed in the second hole 3223 and adapted to engage with the adjusting unit 321 of the adjustment set 32 to thereby adjust a position of the second lens unit 34. Thus, the second lens unit 34 can be adjusted to be moved upwards or downwards through the adjustment set 32. When the adjusting unit 321 is rotated to extend a distance with the locking unit 323, the second lens unit 34 is moved downwards. On the contrary, the second lens unit 34 is moved upwards when the adjusting unit 321 is rotated to shorten a distance with the locking unit 323. Hence, the second lens unit 34 can be situated at a preferable position according to needs.

Referring to FIG. 2, a nose supporting unit 313 is disposed on the frame unit 31 and situated at a place corresponding to a nose bridge of a human and an elastic pad 314 is disposed on a periphery of the frame unit 31 and situated at a place corresponding to a human face. While wearing the goggles 3, the nose supporting unit 313 can fit a nose bridge of a human tightly and support the frame unit 31 effectively, and simultaneously the elastic pad 314 can be in close contact with a human face to thereby prevent the second lens unit 34 from fogging up caused by the exhaled air of the breath of a human. Moreover, the elastic pad 314 can increase the comfort in use. Further, an elastic belt 315 is connected to the frame unit 31 and a regulating buckle 316 is disposed on the elastic belt 315 and adapted to adjust a length of the elastic belt 315. Thus, while wearing the goggles 3, the elastic belt 315 is situated at the back of a human head. The regulating buckle 316 is then moved to adjust a length of the elastic belt 315 whereby the goggles 3 is tightly carried.

Figure 4:
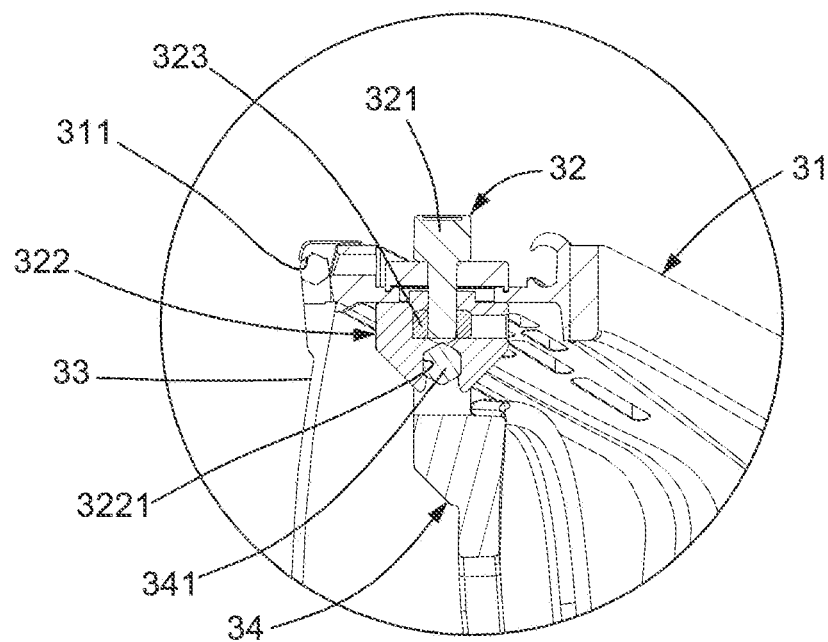
FIG. 4 is a cross-sectional view showing the installation of the frame unit and the first lens unit, and the installation of the second lens unit and the adjustment set.
Figure 5:
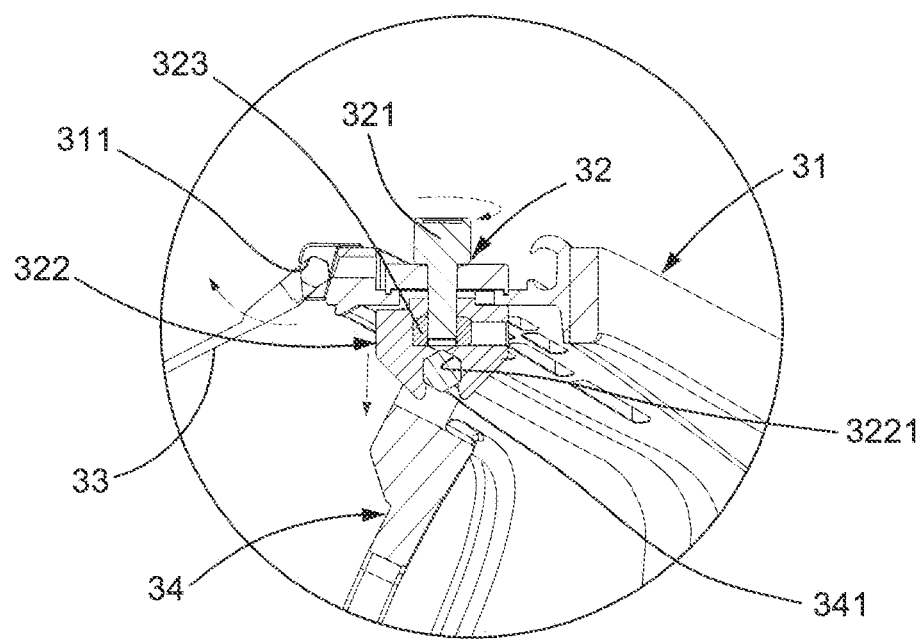
FIG. 5 is a cross-sectional view showing the adjustment of the first lens unit and the second lens unit.

Referring to FIGS. 1, 4 and 5, when using the goggles 3, the frame unit 31 is situated to accommodate the user's eyes and allow the elastic pad 314 to be in close contact with the user's face. Meanwhile, the elastic belt 315 is positioned at the back of the user's head, and the user then adjusts a length of the elastic belt 315 through the regulating buckle 316 to thereby tightly carry the goggles 3. After that, the user rotates the adjusting unit 321 to thereby move the second lens unit 34 upwards or downwards to a proper position corresponding to the eyes. Moreover, the rotation of the engagement portion 341 within the positioning hole 3221 allows the user to lift the second lens unit 34, namely the second lens unit 34 can be lifted open at any angle relative to the frame unit 31, according to needs. Further, the first lens unit 33 can also be lifted open at any angle relative to the frame unit 31 through the rotation within the connecting portion 311 based on requirements. Hence, multiple adjustment is achieved, and the convenience of use is increased.

Figure 6:
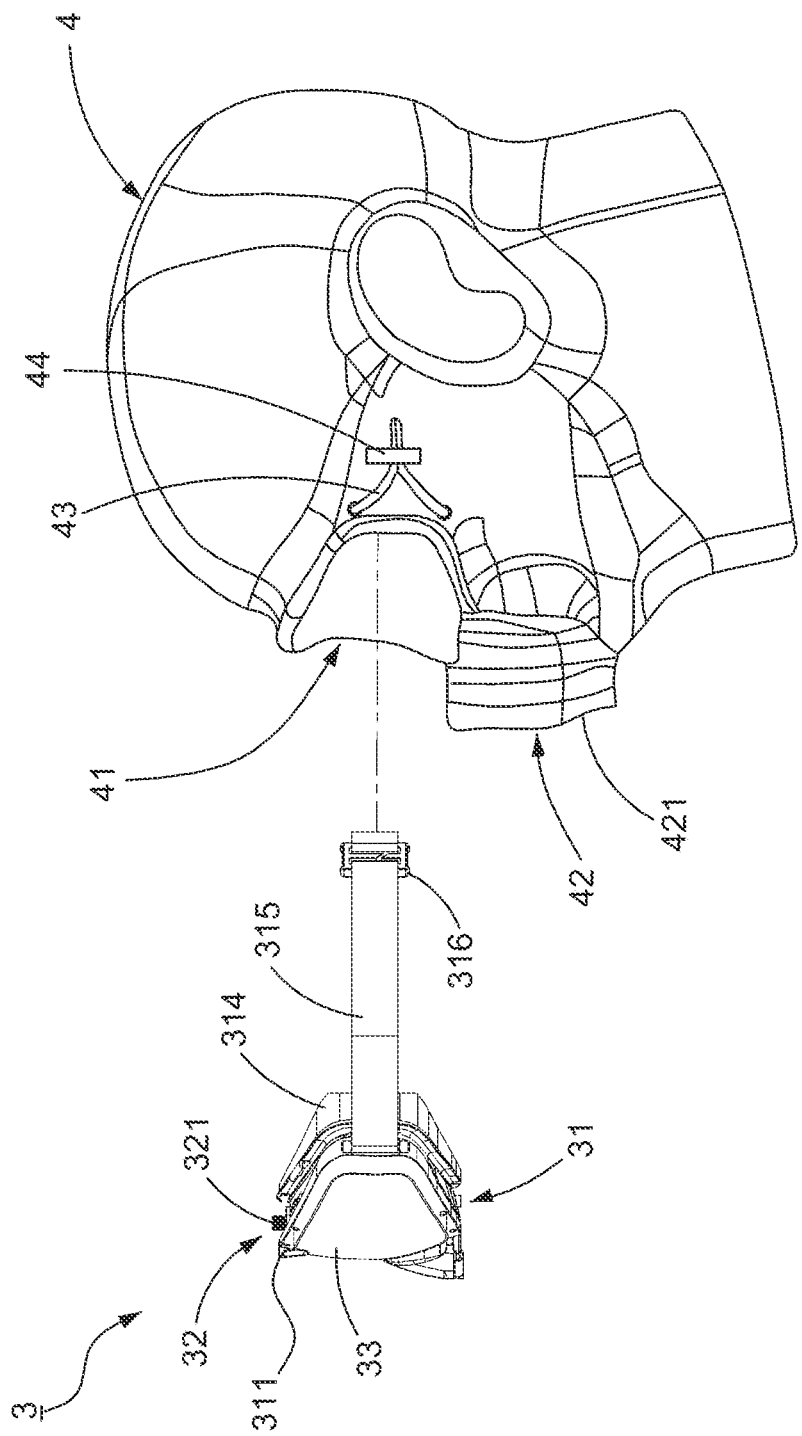
FIG. 6 is a schematic view showing a second preferred embodiment of this invention characterized by a head cover.

FIG. 6 shows a second preferred embodiment of the goggles 3 of this invention. The correlated elements and the concatenation of elements, the operation and objectives of the second preferred embodiment are the same as those of the first preferred embodiment. This embodiment is characterized in that a head cover 4 is connected to the goggles 3. The head cover 4 has a visual region 41 and a breathing region 42. The goggles 3 is installed on the visual region 41 precisely. A periphery of the goggles 3 fits a periphery of the visual region 41 for a close engagement. A breathing mask 421 is disposed on the breathing region 42. The breathing mask 421 is situated at a place corresponding to a human nose while wearing the head cover 4. The head cover 4 further has an elastic rope 43 and a fixing buckle 44 for adjusting an open scope of the visual region 41. The elastic rope 43 is disposed beside the visual region 41 and positioned by the fixing buckle 44. Thus, the user can wear the head cover 4 to cover and protect the head and the mouth, and simultaneously the goggles 3 is adapted to accommodate and protect the eyes and the nose. After that, the user adjusts an open scope of the visual region 41 through tightening or loosening the elastic rope 43 and fixing the elastic rope 43 by the fixing buckle 44. Meanwhile, the breathing mask 421 can support the head cover 4 effectively. The breathing mask 421 will not obstruct the user's breath, namely a proper distance is kept between the breathing mask 421 and the user's nose to thereby ensure smooth breath. Further, the head cover 4 can attain the effect of windproof and sandproof for the user's face.

To sum up, the goggles of this invention take advantages of the adjustment set to move the second lens unit upwards or downwards and lift the second lens unit open at any angle relative to the frame unit. Meanwhile, the pivotal connection of the first lens unit and the frame unit allows the first lens unit to be lifted open at any angle relative to the frame unit. Thus, multiple adjustment is achieved and the convenience of use is increased. Further, the goggles can be connected to the head cover to thereby protect the user's face and head effectively and attain the effect of being windproof and sandproof.

While the embodiments of this invention are shown and described, it is understood that further variations and modifications may be made without departing from the scope of this invention.

What is claimed is:

1. Goggles comprising:
   a frame unit, an adjustment set disposed on said frame unit, a first lens unit pivotally disposed on said frame unit, and a second lens unit disposed on said adjustment set,
   wherein said frame unit includes a connecting portion to which said first lens unit is connected and forms a main hole adapted to engage with said adjustment set, said second lens unit including an engagement portion engaging with said adjustment set, said adjustment set including an adjusting unit penetrating through said main hole and a positioning unit engaging with said adjusting unit,
   wherein a first hole and a second hole communicating with said first hole are respectively formed on said positioning unit, said adjusting unit being inserted into said first hole, said first hole penetrating through said positioning unit by a first penetrating direction, said second hole penetrating through said positioning unit by a second penetrating direction, said first penetrating direction of said first hole being perpendicular to said second penetrating direction of said second hole, a locking unit being disposed in said second hole and adapted to engage with said adjusting unit of said adjustment set to thereby adjust a position of said second lens unit, and wherein a positioning hole being formed on said positioning unit, said engagement portion of said second lens unit being adapted to be rotatably inserted in said positioning hole to thereby connect said second lens unit to said adjustment set pivotally.

2. The goggles according to claim 1, further comprising a nose supporting unit disposed on said frame unit for fitting a nose bridge of a human while wearing said goggles and an elastic pad disposed on a periphery of said frame unit for being in close contact with a human face while wearing said goggles.

3. The goggles according to claim 1, further comprising an elastic belt connected to said frame unit and a regulating buckle disposed on said elastic belt and adapted to adjust a length of said elastic belt.

4. The goggles according to claim 1, further comprising a head cover connected to said goggles, said head cover including a visual region and a breathing region, said goggles being installed on said visual region, a periphery of said goggles fitting a periphery of said visual region for a close engagement.

5. The goggles according to claim 4, wherein said head cover includes an elastic rope and a fixing buckle for adjusting an open scope of said visual region, said elastic rope being disposed beside said visual region and positioned by said fixing buckle.

6. The goggles according to claim 4, further comprising a breathing mask disposed on said breathing region, said breathing mask being situated at a place corresponding to a human nose while wearing said head cover.

* * * * *